United States Patent
Tanaka

(10) Patent No.: US 8,128,910 B2
(45) Date of Patent: Mar. 6, 2012

(54) PESTICIDAL AEROSOL COMPOSITION

(75) Inventor: Yoshito Tanaka, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 329 days.

(21) Appl. No.: 12/593,856

(22) PCT Filed: Mar. 27, 2008

(86) PCT No.: PCT/JP2008/056627
§ 371 (c)(1), (2), (4) Date: Sep. 29, 2009

(87) PCT Pub. No.: WO2008/123564
PCT Pub. Date: Oct. 16, 2008

(65) Prior Publication Data
US 2010/0047183 A1    Feb. 25, 2010

(30) Foreign Application Priority Data
Mar. 30, 2007    (JP) ................. 2007-091204

(51) Int. Cl.
*A01N 53/02* (2006.01)
*A01N 53/06* (2006.01)
*A01N 53/08* (2006.01)
*A01N 25/06* (2006.01)
*A01P 7/04* (2006.01)

(52) U.S. Cl. ............. 424/43; 424/45; 514/521; 514/531

(58) Field of Classification Search .......... 514/521, 514/531; 424/43, 45
See application file for complete search history.

(56) References Cited

U.S. PATENT DOCUMENTS
6,908,945 B2    6/2005    Mori
7,217,682 B2 *  5/2007    Mori .................. 504/309

2003/0195119 A1    10/2003    Mori
2004/0037782 A1    2/2004    Hernandez et al.

FOREIGN PATENT DOCUMENTS
EP              1 462 441 A1    9/2004
WO    WO 2005/070210    *    8/2005

OTHER PUBLICATIONS

Singapore Search and Examination Report, dated Aug. 17, 2010, for Singapore Application No. 200906025-2.

* cited by examiner

*Primary Examiner* — John Pak
(74) *Attorney, Agent, or Firm* — Birch, Stewart, Kolasch & Birch, LLP

(57) ABSTRACT

A pesticidal aerosol composition, containing 3-phenoxybenzyl ester compound represented by Formula (I):

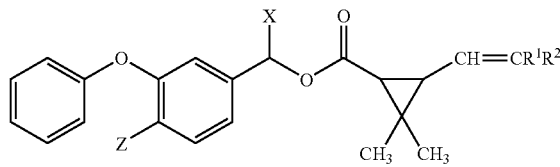

(I)

wherein, X represents a hydrogen atom or a cyano group; Z represents a hydrogen atom or a fluorine atom; and $R^1$ and $R^2$ each independently represent a hydrogen atom, a C1-C3 alkyl group that may be substituted with halogen atoms, or a halogen atom;

4-methoxymethyl-2,3,5,6-tetrafluorobenzyl 3-(2-cyano-1-propenyl)-2,2-dimethylcyclopropanecarboxylate, an organic solvent, and a propellant has an excellent pesticidal activity.

9 Claims, No Drawings

PESTICIDAL AEROSOL COMPOSITION

This application is a 371 of PCT/JP2008/056627, filed on Mar. 27, 2008.

FIELD OF THE INVENTION

The present invention relates to a pesticidal aerosol composition.

DESCRIPTION OF THE RELATED ART

4-Methoxymethyl-2,3,5,6-tetrafluorobenzyl 3-(2-cyano-1-propenyl)-2,2-dimethylcyclopropanecarboxylate is known to have a pesticidal activity (e.g., U.S. Pat. No. 6,908,945).

SUMMARY OF THE INVENTION

An object of the present invention is to provide an aerosol composition having an excellent pesticidal activity.

After intensive studies to find an aerosol composition superior in pesticidal activity, the inventors have found that an aerosol containing a pesticidal aerosol composition which contains: a 3-phenoxybenzyl ester compound represented by Formula (I):

$$\text{(I)}$$

wherein, X represents a hydrogen atom or a cyano group; Z represents a hydrogen atom or a fluorine atom; and $R^1$ and $R^2$ each independently represent a hydrogen atom, a $C_1$-$C_3$ alkyl group that may be substituted with halogen atoms, or a halogen atom;

4-methoxymethyl-2,3,5,6-tetrafluorobenzyl 3-(2-cyano-1-propenyl)-2,2-dimethylcyclopropanecarboxylate;

an organic solvent; and a propellant has an excellent pesticidal activity, and thus, achieved the present invention.

The present invention provides:

[1] A pesticidal aerosol composition, comprising:

a 3-phenoxybenzyl ester compound represented by Formula (I):

$$\text{(I)}$$

wherein, X represents a hydrogen atom or a cyano group; Z represents a hydrogen atom or a fluorine atom; and $R^1$ and $R^2$ each independently represent a hydrogen atom, a $C_1$-$C_3$ alkyl group that may be substituted with halogen atoms, or a halogen atom;

4-methoxymethyl-2,3,5,6-tetrafluorobenzyl 3-(2-cyano-1-propenyl)-2,2-dimethylcyclopropanecarboxylate;

an organic solvent; and a propellant;

[2] The pesticidal aerosol composition described in [1], wherein Z in Formula (I) is a hydrogen atom;

[3] The pesticidal aerosol composition described in [1] or [2], wherein the composition comprises the 3-phenoxybenzyl ester compound represented by Formula (I) in an amount of 0.5 to 50 parts by weight per part by weight of 4-methoxymethyl-2,3,5,6-tetrafluorobenzyl 3-(2-cyano-1-propenyl)-2,2-dimethylcyclopropanecarboxylate;

[4] The pesticidal aerosol composition described in any one of [1] to [3], wherein the composition comprises the 3-phenoxybenzyl ester compound represented by Formula (I) and 4-methoxymethyl-2,3,5,6-tetrafluorobenzyl 3-(2-cyano-1-propenyl)-2,2-dimethylcyclopropanecarboxylate in a total amount of 0.001 to 1% by weight, the organic solvent in an amount of 10 to 79% by weight, and the propellant in an amount of 20 to 80% by weight;

[5] The pesticidal aerosol composition described in any one of [1] to [4], wherein the 3-phenoxybenzyl ester compound represented by Formula (I) is at least one compound selected from the group consisting of phenothrin, cyphenothrin, permethrin, cypermethrin, cyfluthrin and deltamethrin;

[6] The pesticidal aerosol composition described in any one of [1] to [5], wherein the 3-phenoxybenzyl ester compound represented by Formula (I) is at least one compound selected from the group consisting of phenothrin, cyphenothrin, permethrin, cypermethrin and deltamethrin;

[7] The pesticidal aerosol composition described in any one of [1] to [6], wherein the organic solvent comprises a saturated hydrocarbon solvent;

[8] The pesticidal aerosol composition described in [7], wherein the organic solvent comprises a saturated hydrocarbon solvent in an amount of 70 to 100% by weight;

[9] The pesticidal aerosol composition described in any one of [1] to [8], wherein the composition is for controlling flies; and

[10] A pesticidal aerosol comprising the pesticidal aerosol composition described in any one of [1] to [9].

It is possible to control harmful insects by using the pesticidal aerosol composition according to the present invention.

DETAILED DESCRIPTION OF THE INVENTION

The pesticidal aerosol composition according to the present invention comprises a 3-phenoxybenzyl ester compound (hereinafter, referred to as the Ester compound in some cases) represented by Formula (I):

$$\text{(I)}$$

wherein, X represents a hydrogen atom or a cyano group; Z represents a hydrogen atom or a fluorine atom; and $R^1$ and $R^2$ each independently represent a hydrogen atom, a $C_1$-$C_3$ alkyl group that may be substituted with halogen atoms, or a halogen atom;

4-methoxymethyl-2,3,5,6-tetrafluorobenzyl 3-(2-cyano-1-propenyl)-2,2-dimethylcyclopropanecarboxylate (hereinafter, referred to as the compound A in some cases),
an organic solvent and
a propellant.

Examples of the Ester compounds include phenothrin (X=H, $R^1$=CH$_3$, $R^2$=CH$_3$), cyphenothrin (X=CN, $R^1$=CH$_3$, $R^2$=CH$_3$), permethrin (X=H, $R^1$=Cl, $R^2$=Cl), cypermethrin (X=CN, $R^1$=Cl, $R^2$=Cl) and deltamethrin (X=CN, $R^1$=Br, $R^2$=Br) represented by Formula (Ia)

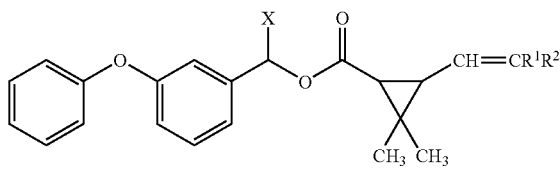

(Ia)

and cyfluthrin (X=CN, $R^1$=Cl, $R^2$=Cl) represented by Formula (Ib):

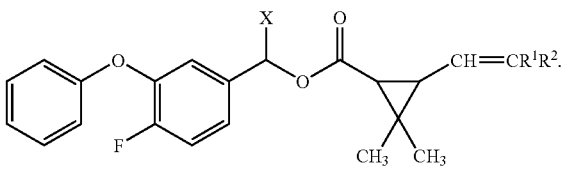

(Ib)

The Ester compound has isomers, attributable to the two asymmetric carbon atoms in the cyclopropane ring, the asymmetric carbon atom bound to a cyano group when X represents a cyano group, and the double bond when $R^1$ and $R^2$ represent different groups, but each isomer or any mixture at an arbitrary isomer ratio may be used as the Ester compound according to the present invention.

The compound A is, for example, a compound described in U.S. Pat. No. 6,908,945, and can be prepared according to a method described therein.

The compound A has isomers, attributable to the two asymmetric carbons atoms and the double bond present in the cyclopropane ring, but each isomer or a mixture thereof at an arbitrary isomer ratio may be used as the compound A according to the present invention.

The total content of the Ester compound and the compound A contained in the pesticidal aerosol composition according to the present invention is usually 0.001 to 50% by weight, preferably 0.01 to 1% by weight. As for the content rate of the Ester compound to the compound A contained in the pesticidal aerosol composition according to the present invention, the Ester compound is used usually in an amount of 0.5 to 50 parts by weight, preferably 0.5 to 30 parts by weight, per part by weight of the compound A.

Examples of the organic solvents contained in the pesticidal aerosol composition according to the present invention include normal paraffin solvents such as Neochiozol (manufactured by Chuokasei Co., Ltd.), Norpar 13 (manufactured by Exxon Mobil Corp.), and Norpar 15 (manufactured by Exxon Mobil Corp.); isoparaffin solvents such as Isopar G (manufactured by Exxon Mobil Corp.), Isopar L (manufactured by Exxon Mobil Corp.), Isopar H (Exxon Mobil Corp.) and Isopar M (Exxon Mobil Corp.); and the mixture thereof; and saturated hydrocarbon solvents, for example, mixtures of naphthene (cycloparaffin) with a linear saturated hydrocarbon such as Exxsol D40 (manufactured by Exxon Mobil Corp.), Exxsol D60 (manufactured by Exxon Mobil Corp.), or Exxsol D80 (manufactured by Exxon Mobil Corp.). When the organic solvent contains saturated hydrocarbon solvents, the content of the saturated hydrocarbon solvents in the organic solvent is preferably, for example, about 70 to 100% by weight.

The content of the organic solvents in the pesticidal aerosol composition according to the present invention is usually 10 to 79% by weight, preferably 20 to 70% by weight.

The propellant contained in the pesticidal aerosol composition according to the present invention is a liquefied gas having a boiling point of from −50° C. to 0° C., and examples of the propellants include liquefied petroleum gas (LPG), dimethylether, propane, n-butane and isobutane. The content of the propellant in the pesticidal aerosol composition according to the present invention is usually 20 to 80% by weight, preferably 25 to 75% by weight.

The pesticidal aerosol composition according to the present invention may contain, as needed, one or more of additional additives such as other pesticidal components, repellents, synergists, and flavoring agents.

Examples of the other pesticidal components include organophosphates such as dichlorvos, fenitrothion, tetrachlorvinphos, fenthion, chlorpyrifos and diazinon; carbamate compounds such as propoxur, carbaryl, metoxadiazone, and fenobucarb; chitin synthesis inhibitors such as lufenuron, chlorfluazuron, hexaflumuron, diflubenzuron, cyromazine, and 1-(2,6-difluorobenzoyl)-3-[2-fluoro-4-(1,1,2,3,3,3-hexafluoropropoxy)phenyl]urea; juvenile hormone analogs such as pyriproxyfen, methoprene, hydroprene, and fenoxycarb; neonicotinoids; and N-phenylpyrazoles.

Examples of the repellents include N,N-diethyl-m-toluamide, limonene, linalool, citronellal, menthol, menthone, hinokitiol, geraniol, eucalyptol, indoxacarb, carane-3,4-diol, MGK-R-326, MGK-R-874, and BAY-KBR-3023.

Examples of the synergists include 5-[2-(2-butoxyethoxy)ethoxymethyl]-6-propyl-1,3-benzodioxol, N-(2-ethylhexyl)bicyclo[2.2.1]hept-5-ene-2,3-dicarboxylmide, octachlorodipropylether, isobornylthiocyanoacetate, and N-(2-ethylhexyl)-1-isopropyl-4-methylbicyclo[2.2.2]oct-5-ene-2,3-dicarboxylmide.

Examples of the stabilizers include phenolic antioxidants such as 2,6-di-t-butyl-4-methylphenol.

A pesticidal aerosol containing the pesticidal aerosol composition according to the present invention can be prepared, for example, by filling an aerosol container with the ester compound, the compound A and an organic solvent and as needed other additives such as a pesticidal component, a repellent, a synergist, and a stabilizer, attaching an aerosol valve to the container, filling the container with a propellant through the stem and shaking the container, followed by installing an actuator additionally. Examples of the actuators include push-button and trigger actuators.

The pesticidal aerosol composition according to the present invention is used, for example, by spraying a pesticidal aerosol containing an effective amount of the pesticidal aerosol composition according to the present invention on harmful insects and the migration route and/or the locus where the insects inhabit. The spraying amount then is usually approximately 0.001 to 1,000 mg per m$^2$ as the total amount of the Ester compound and the compound A when applied on an area, and usually approximately 0.001 to 1,000 mg per 1 m$^3$ the total amount of the Ester compound and the compound A when applied in a space.

The pesticidal aerosol composition according to the present invention is effective for control of the following harmful insects such as flies and cockroaches, and acarines: cockroaches such as *Blattella germanica, Periplaneta fuliginosa*, and *Periplaneta americana*; flies such as *Musca domestica* and *Muscina stabulans*; mosquitos such as *Culex pipiens pallens, Culex tritaeniorhynchus, Culex pipiens quinquefasciatus*, and *Aedes albopictus*; acarines such as *Tyrophagus putrescentiae, Dermatophagoides farinae, Cheyletus malaccensis, Chelacaropsis moorei, Haemaphysalis longicornis, Ixodes ovatus*, and *Boophilus microplus*; anoplurae such as *Pediculus humanus* and *Haematopinus eurysternus*; termites such as *Reticulitermes speratus speratus* and *Coptotermes formosanus*; bark beetles; Chironomidae; Psychodidae; ants; bees; and fleas such as *Ctenocephalides felis, Ctenocephalides canis, Pulex irritans*, and *Xenopsylla cheopis*.

EXAMPLES

Hereinafter, the present invention will be described in more detail with reference to Formulation Examples and Test Examples, etc., but it should be understood that the present invention is not restricted thereto.

First, Formulation Examples for the aerosols containing the pesticidal aerosol composition according to the present invention will be described. "Part" in the following Examples means "part by weight".

Formulation Example 1

0.01 part of 4-methoxymethyl-2,3,5,6-tetrafluorobenzyl (1R)-trans-3-(2-cyano-1-propenyl(E/Z=1/5))-2,2-dimethyl-cyclopropanecarboxylate, 0.15 part of permethrin, 5 parts of dichloromethane and 34.84 parts of Isopar M (manufactured by Exxon Mobil Corp.) were placed in an aerosol can. Then, a valve was attached to the can, and 60 parts of a propellant (liquefied petroleum gas) was charged through the valve into the can, to give an aerosol containing 100 parts of the pesticidal aerosol composition (hereinafter, referred to as inventive aerosol (1)).

Formulation Example 2

0.01 part of 4-methoxymethyl-2,3,5,6-tetrafluorobenzyl (1R)-trans-3-(2-cyano-1-propenyl(E/Z=1/5))-2,2-dimethyl-cyclopropanecarboxylate, 0.1 part of phenothrin, 5 parts of dichloromethane and 34.89 parts of Isopar M (manufactured by Exxon Mobil Corp.) were placed in an aerosol can. Then, a valve was attached to the can, and 60 parts of a propellant (liquefied petroleum gas) was charged through the valve into the can, to give an aerosol containing 100 parts of the pesticidal aerosol composition (hereinafter, referred to as inventive aerosol (2)).

Formulation Example 3

0.01 part of 4-methoxymethyl-2,3,5,6-tetrafluorobenzyl (1R)-trans-3-(2-cyano-1-propenyl(E/Z=1/5))-2,2-dimethyl-cyclopropanecarboxylate, 0.05 part of cyphenothrin, 5 parts of dichloromethane and 34.94 parts of Isopar M (manufactured by Exxon Mobil Corp.) were placed in an aerosol can. Then, a valve was attached to the can, and 60 parts of a propellant (liquefied petroleum gas) was charged through the valve into the can, to give an aerosol containing 100 parts of the pesticidal aerosol composition (hereinafter, referred to as inventive aerosol (3)).

Formulation Example 4

0.01 part of 4-methoxymethyl-2,3,5,6-tetrafluorobenzyl (1R)-trans-3-(2-cyano-1-propenyl(E/Z=1/5))-2,2-dimethyl-cyclopropanecarboxylate, 0.1 part of cypermethrin, 5 parts of dichloromethane and 34.89 parts of Isopar M (manufactured by Exxon Mobil Corp.) were placed in an aerosol can. Then, a valve was attached to the can, and 60 parts of a propellant (liquefied petroleum gas) was charged through the valve into the can, to give an aerosol containing 100 parts of the pesticidal aerosol composition (hereinafter, referred to as inventive aerosol (4)).

Formulation Example 5

0.01 part of 4-methoxymethyl-2,3,5,6-tetrafluorobenzyl (1R)-trans-3-(2-cyano-1-propenyl(E/Z=1/5))-2,2-dimethyl-cyclopropanecarboxylate, 0.05 part of deltamethrin, 5 parts of dichloromethane and 34.94 parts of Isopar M (manufactured by Exxon Mobil Corp.) were placed in an aerosol can. Then, a valve was attached to the can, and 60 parts of a propellant (liquefied petroleum gas) was charged through the valve into the can, to give an aerosol containing 100 parts of the pesticidal aerosol composition (hereinafter, referred to as inventive aerosol (5)).

Formulation Example 6

0.01 part of 4-methoxymethyl-2,3,5,6-tetrafluorobenzyl (1R)-trans-3-(2-cyano-1-propenyl(E/Z=1/5))-2,2-dimethyl-cyclopropanecarboxylate, 0.1 part of cyfluthrin, 5 parts of dichloromethane and 34.89 parts of Isopar M (manufactured by Exxon Mobil Corp.) are placed in an aerosol can. Then, a valve is attached to the can, and 60 parts of a propellant (liquefied petroleum gas) is charged through the valve into the can, to give an aerosol containing 100 parts of the pesticidal aerosol composition (hereinafter, referred to as inventive aerosol (6)).

Formulation Example 7

0.01 part of 4-methoxymethyl-2,3,5,6-tetrafluorobenzyl (1R)-trans-3-(2-cyano-1-propenyl(E/Z=1/5))-2,2-dimethyl-cyclopropanecarboxylate, 0.15 part of permethrin and 59.84 parts of Isopar M (manufactured by Exxon Mobil Corp.) were placed in an aerosol can. Then, a valve was attached to the can, and 40 parts of a propellant (liquefied petroleum gas) was charged through the valve into the can, to give an aerosol containing 100 parts of the pesticidal aerosol composition (hereinafter, referred to as inventive aerosol (7)).

Reference Preparative Example 1

0.01 part of 4-methoxymethyl-2,3,5,6-tetrafluorobenzyl (1R)-trans-3-(2-cyano-1-propenyl(E/Z=1/5))-2,2-dimethyl-cyclopropanecarboxylate, 5 parts of dichloromethane and 34.99 parts of Isopar M (manufactured by Exxon Mobil Corp.) were placed in an aerosol can. Then, a valve was attached to the can, and 60 parts of a propellant (liquefied petroleum gas) was charged through the valve into the can, to give an aerosol containing 100 parts of the aerosol composition (hereinafter, referred to as comparative aerosol (1)).

Reference Preparative Example 2

0.15 part of permethrin, 5 parts of dichloromethane and 34.85 parts of Isopar M (manufactured by Exxon Mobil Corp.) were placed in an aerosol can. Then, a valve was attached to the can, and 60 parts of a propellant (liquefied petroleum gas) was charged through the valve into the can, to give an aerosol containing 100 parts of the aerosol composition (hereinafter, referred to as comparative aerosol (2)).

Reference Preparative Example 3

0.1 part of phenothrin, 5 parts of dichloromethane and 34.9 parts of Isopar M (manufactured by Exxon Mobil Corp.) were placed in an aerosol can. Then, a valve was attached to the can, and 60 parts of a propellant (liquefied petroleum gas) was charged through the valve into the can, to give an aerosol containing 100 parts of the aerosol composition (hereinafter, referred to as comparative aerosol (3)).

Reference Preparative Example 4

0.05 part of cyphenothrin, 5 parts of dichloromethane and 34.95 parts of Isopar M (manufactured by Exxon Mobil Corp.) were placed in an aerosol can. Then, a valve was attached to the can, and 60 parts of a propellant (liquefied petroleum gas) was charged through the valve into the can, to give an aerosol containing 100 parts of the aerosol composition (hereinafter, referred to as comparative aerosol (4)).

Reference Preparative Example 5

0.1 part of cypermethrin, 5 parts of dichloromethane and 34.9 parts of Isopar M (manufactured by Exxon Mobil Corp.) were placed in an aerosol can. Then, a valve was attached to the can, and 60 parts of a propellant (liquefied petroleum gas) was charged through the valve into the can, to give an aerosol containing 100 parts of the aerosol composition (hereinafter, referred to as comparative aerosol (5)).

Reference Preparative Example 6

0.05 part of Deltamethrin, 5 parts of dichloromethane and 34.95 parts of Isopar M (manufactured by Exxon Mobil Corp.) were placed in an aerosol can. Then, a valve was attached to the can, and 60 parts of a propellant (liquefied petroleum gas) was charged through the valve into the can, to give an aerosol containing 100 parts of the aerosol composition (hereinafter, referred to as comparative aerosol (6)).

Reference Preparative Example 7

0.01 part of 4-methoxymethyl-2,3,5,6-tetrafluorobenzyl (1R)-trans-3-(2-cyano-1-propenyl(E/Z=1/5))-2,2-dimethyl-cyclopropanecarboxylate, 0.1 part of fenitrothion, 5 parts of dichloromethane and 34.89 parts of Isopar M (manufactured by Exxon Mobil Corp.) were placed in an aerosol can. Then, a valve was attached to the can, and 60 parts of a propellant (liquefied petroleum gas) was charged through the valve into the can, to give an aerosol containing 100 parts of the aerosol composition (hereinafter, referred to as comparative aerosol (7)).

Reference Preparative Example 8

0.01 part of 4-methoxymethyl-2,3,5,6-tetrafluorobenzyl (1R)-trans-3-(2-cyano-1-propenyl(E/Z=1/5))-2,2-dimethyl-cyclopropanecarboxylate, 0.1 part of ethofenprox, 5 parts of dichloromethane and 34.89 parts Isopar M (manufactured by Exxon Mobil Corp.) were placed in an aerosol can. Then, a valve was attached to the can, and 60 parts of a propellant (liquefied petroleum gas) was charged through the valve into the can, to give an aerosol containing 100 parts of the aerosol composition (hereinafter, referred to as comparative aerosol (8)).

Reference Preparative Example 9

0.01 part of 4-methoxymethyl-2,3,5,6-tetrafluorobenzyl (1R)-trans-3-(2-cyano-1-propenyl(E/Z=1/5))-2,2-dimethyl-cyclopropanecarboxylate, 0.1 part of bifenthrin, 5 parts of dichloromethane and 34.89 parts of Isopar M (manufactured by Exxon Mobil Corp.) were placed in an aerosol can. Then, a valve was attached to the can, and 60 parts of a propellant (liquefied petroleum gas) was charged through the valve into the can, to give an aerosol containing 100 parts of the aerosol composition (hereinafter, referred to as comparative aerosol (9)).

Reference Preparative Example 10

0.1 part of fenitrothion, 5 parts of dichloromethane and 34.9 parts of Isopar M (manufactured by Exxon Mobil Corp.) were placed in an aerosol can. Then, a valve was attached to the can, and 60 parts of a propellant (liquefied petroleum gas) was charged through the valve into the can, to give an aerosol containing 100 parts of the aerosol composition (hereinafter, referred to as comparative aerosol (10)).

Reference Preparative Example 11

0.1 part of ethofenprox, 5 parts of dichloromethane and 34.9 parts of Isopar M (manufactured by Exxon Mobil Corp.) were placed in an aerosol can. Then, a valve was attached to the can, and 60 parts of a propellant (liquefied petroleum gas) was charged through the valve into the can, to give an aerosol containing 100 parts of the aerosol composition (hereinafter, referred to as comparative aerosol (11)).

Reference Preparative Example 12

0.1 part of bifenthrin, 5 parts of dichloromethane and 34.9 parts of Isopar M (manufactured by Exxon Mobil Corp.) were placed in an aerosol can. Then, a valve was attached to the can, and 60 parts of a propellant (liquefied petroleum gas) was charged through the valve into the can, to give an aerosol containing 100 parts of the aerosol composition (hereinafter, referred to as comparative aerosol (12)).

Hereinafter, the excellent pesticidal effects of the aerosols containing the pesticidal aerosol composition according to the present invention will be described in Test Examples.

Test Example 1

Ten adult houseflies (five males and females) were placed in a polyethylene cup (bottom diameter: 10.6 cm, top diameter: 12 cm, height: 7 cm), and the cup was covered with a 16-mesh nylon gauze. Separately, a cup containing no housefly was provided. The cup containing houseflies was placed on the center of the bottom face of a 70-cm cubic chamber, and the cap without housefly was placed on the rear side of the bottom face.

The inventive aerosol (1) was sprayed into the chamber through a window formed in the center of the front side wall of the chamber, in an amount of 300 mg as an aerosol composition. Then, the number of the houseflies knocked down was counted over a period of 10 minutes. The knock down rate (KD rate) 7 minutes after the spraying was determined.

Test Examples 2 to 5

The same procedures as in Test Example 1 were repeated except that the inventive aerosol (1) was replaced with the inventive aerosols (2) to (5).

Reference Test Examples 1 to 6

The same procedures as in Test Example 1 were repeated except that the inventive aerosol (1) was replaced with the comparative aerosols (1) to (6).

The results obtained in Test Examples 1 to 5 and Reference Test Examples 1 to 6 are summarized in Table 1.

TABLE 1

| Test number | Compound A content (wt %) | Ester compound Compound name | Ester compound Content | KD rate (%) |
|---|---|---|---|---|
| Test Example 1 | 0.01 | Permethrin | 0.15 | 80 |
| Test Example 2 | 0.01 | Phenothrin | 0.1 | 75 |
| Test Example 3 | 0.01 | Cyphenothrin | 0.05 | 75 |
| Test Example 4 | 0.01 | Cypermethrin | 0.1 | 80 |
| Test Example 5 | 0.01 | Deltamethrin | 0.05 | 85 |
| Reference Test Example 1 | 0.01 | — | — | 15 |
| Reference Test Example 2 | — | Permethrin | 0.15 | 0 |
| Reference Test Example 3 | — | Phenothrin | 0.1 | 0 |
| Reference Test Example 4 | — | Cyphenothrin | 0.05 | 0 |
| Reference Test Example 5 | — | Cypermethrin | 0.1 | 35 |
| Reference Test Example 6 | — | Deltamethrin | 0.05 | 40 |

Reference Test Examples 7 to 12

The same procedures as in Test Example 1 were repeated except that the inventive aerosol (1) was replaced with the comparative aerosols (7) to (12).

The results are summarized in Table 2.

TABLE 2

| Test number | Compound A content (wt %) | Other pesticidal compound Compound name | Other pesticidal compound Content | KD rate (%) |
|---|---|---|---|---|
| Reference Test Example 7 | 0.01 | Fenitrothion | 0.1 | 10 |
| Reference Test Example 8 | 0.01 | Ethofenprox | 0.1 | 10 |
| Reference Test Example 9 | 0.01 | Bifenthrin | 0.1 | 20 |
| Reference Test Example 10 | — | Fenitrothion | 0.1 | 0 |
| Reference Test Example 11 | — | Ethofenprox | 0.1 | 0 |
| Reference Test Example 12 | — | Bifenthrin | 0.1 | 0 |

Aerosols containing a pesticidal aerosol composition containing both of the compound A and the Ester compound were shown to have an outstandingly higher pesticidal activity than that of the aerosols containing an aerosol composition containing either the compound A or the Ester compound.

On the other hand, aerosols containing an aerosol composition containing the compound A and a pesticidal compound other than the Ester compound were shown to have no such improvement in pesticidal activity, compared to the aerosol containing an aerosol composition containing the pesticidal compound alone.

Test Example 6

Ten cockroaches Blattella germanica (5 males and 5 females) were released in a test container with butter applied on the internal wall (diameter: 8.75 cm, height: 7.5 cm, bottom face: 16 mesh metal gauze). The container was placed at the inner bottom of a cylindrical chamber having an inner diameter of 16.5 cm and a height of 60 cm. 400 Milligrams of the inventive aerosol (7) was sprayed onto the cup from the top opening of the chamber. Thereafter, the knocked-down insects were counted along a passage of time up to the expiration of 5 minutes.

From the results, the time needed for knocking down 50% of the tested insects ($KT_{50}$) was determined (each in duplicate). As a result, $KT_{50}$ was 1.5 minutes.

Test Example 7

Six cockroaches Periplaneta fuliginosa (3 males and 3 females) were released in a test container with butter applied on the internal wall (diameter: 12.5 cm, height: 10 cm, bottom face: 43 mesh metal gauze). The container was placed at the inner bottom of a cylindrical chamber having an inner diameter of 16.5 cm and a height of 60 cm. 1000 Milligrams of the inventive aerosol (7) was sprayed onto the cup from the top opening of the chamber. Thereafter, the knocked-down insects were counted along a passage of time up to the expiration of 20 minutes. From the results, the time needed for knocking down 50% of the tested insects ($KT_{50}$) was determined (each in duplicate). As a result, $KT_{50}$ was 16 minutes.

The invention claimed is:

1. A pesticidal aerosol composition, comprising:
   a 3-phenoxybenzyl ester compound represented by Formula (I):

$$\text{(I)}$$

wherein, X represents a hydrogen atom or a cyano group; Z represents a hydrogen atom or a fluorine atom; and $R^1$ and $R^2$ each independently represent a hydrogen atom, a $C_1$-$C_3$ alkyl group which may be substituted with at least one halogen atom, or a halogen atom;

4-methoxymethyl-2,3,5,6-tetrafluorobenzyl 3-(2-cyano-1-propenyl)-2,2-dimethylcyclopropanecarboxylate;
   an organic solvent; and
   a propellant.

2. The pesticidal aerosol composition according to claim 1, wherein Z in Formula (I) is a hydrogen atom.

3. The pesticidal aerosol composition according to claim 1 or 2, wherein the composition comprises the 3-phenoxybenzyl ester compound represented oy Formula (I) in an amount of 0.5 to 50 parts by weight per part by weight of 4-methoxymethyl-2,3,5,6-tetrafluorobenzyl 3-(2-cyano-1-propenyl)-2,2-dimethylcyclopropanecarboxylate.

4. The pesticidal aerosol composition according to claim 1, wherein the composition comprises the 3-phenoxybenzyl ester compound represented by Formula (I) and 4-methoxymethyl-2,3,5,6-tetrafluorobenzyl 3-(2-cyano-1-propenyl)-2,2-dimethylcyclopropanecarboxylate in a total amount of 0.001 to 1% by weight, the organic solvent in an amount of 10 to 79% by weight, and the propellant in an amount of 20 to 80% by weight.

5. The pesticidal aerosol composition according to claim 1, wherein the 3-phenoxybenzyl ester compound represented by Formula (I) is at least one compound selected from the group consisting of phenothrin, cyphenothrin, permethrin, cypermethrin, cyfluthrin and deltamethrin.

6. The pesticidal aerosol composition according to claim 1, wherein the 3-phenoxybenzyl ester compound represented by Formula (I) is at least one compound selected from the group consisting of phenothrin, cyphenothrin, permethrin, cypermethrin and deltamethrin.

7. The pesticidal aerosol composition according to claim 1, wherein the organic solvent comprises a saturated hydrocarbon solvent.

8. The pesticidal aerosol composition according to claim 7, wherein the organic solvent comprises a saturated hydrocarbon solvent in an amount of at least 70% by weight.

9. A method of controlling flies which comprises spraying the pesticidal aerosol composition according to claim 1 on flies.

* * * * *

UNITED STATES PATENT AND TRADEMARK OFFICE
CERTIFICATE OF CORRECTION

| | | |
|---|---|---|
| PATENT NO. | : 8,128,910 B2 | Page 1 of 1 |
| APPLICATION NO. | : 12/593856 | |
| DATED | : March 6, 2012 | |
| INVENTOR(S) | : Yoshito Tanaka | |

It is certified that error appears in the above-identified patent and that said Letters Patent is hereby corrected as shown below:

In claim 3, at column 10, line 66, change "oy Formula (I)" to --by Formula (I)--.

Signed and Sealed this
Eleventh Day of December, 2012

David J. Kappos
*Director of the United States Patent and Trademark Office*